(12) United States Patent
Ein-Gal

(10) Patent No.: US 7,893,412 B2
(45) Date of Patent: Feb. 22, 2011

(54) ATTENUATOR SYSTEM FOR BEAM MODULATION

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 167 days.

(21) Appl. No.: 12/324,868

(22) Filed: Nov. 27, 2008

(65) Prior Publication Data
US 2010/0127192 A1 May 27, 2010

(51) Int. Cl.
*G21K 1/04* (2006.01)
(52) U.S. Cl. ............ 250/505.1; 250/492.1; 250/492.23; 250/492.3
(58) Field of Classification Search ............ 250/492.1, 250/492.23, 492.3, 505.1
See application file for complete search history.

(56) References Cited

U.S. PATENT DOCUMENTS

| | | | | |
|---|---|---|---|---|
| 5,019,713 A * | 5/1991 | Schmidt | | 250/492.3 |
| 5,440,133 A * | 8/1995 | Moyers et al. | | 250/492.3 |
| 6,266,393 B1 * | 7/2001 | Ein-Gal | | 378/152 |
| 6,389,108 B1 * | 5/2002 | Ein-Gal | | 378/147 |
| 6,526,123 B2 * | 2/2003 | Ein-Gal | | 378/152 |
| 6,617,598 B1 * | 9/2003 | Matsuda | | 250/492.3 |
| 7,449,701 B2 * | 11/2008 | Fujimaki et al. | | 250/492.3 |
| 2001/0043669 A1 * | 11/2001 | Ein-Gal | | 378/152 |
| 2004/0000650 A1 * | 1/2004 | Yanagisawa et al. | | 250/492.3 |
| 2005/0058245 A1 * | 3/2005 | Ein-Gal | | 378/65 |
| 2006/0173294 A1 * | 8/2006 | Ein-Gal | | 600/427 |
| 2006/0192146 A1 * | 8/2006 | Yanagisawa et al. | | 250/492.1 |
| 2007/0228304 A1 * | 10/2007 | Nishiuchi et al. | | 250/505.1 |
| 2009/0283704 A1 * | 11/2009 | Nishiuchi et al. | | 250/492.3 |

* cited by examiner

*Primary Examiner*—Jack I Berman
*Assistant Examiner*—Michael Maskell
(74) *Attorney, Agent, or Firm*—Dekel Patent Ltd.; David Klein

(57) ABSTRACT

An attenuator system for attenuating a radiation beam, including a first attenuating element placed in a path of a radiation beam for attenuation thereof, a second attenuating element placed distal to the first attenuating element for further attenuation of the radiation beam, a first positioner operatively connected to the first attenuating element, which moves the first attenuating element along a first direction, a first processor operatively connected to the first positioner for controlling motion of the first attenuating element, a second positioner operatively connected to the second attenuating element, which moves the second attenuating element along a second direction, and a second processor operatively connected to the second positioner for controlling motion of the second attenuating element, wherein a two-dimensional attenuation distribution of the first attenuating element varies linearly with respect to at least one coordinate.

17 Claims, 1 Drawing Sheet

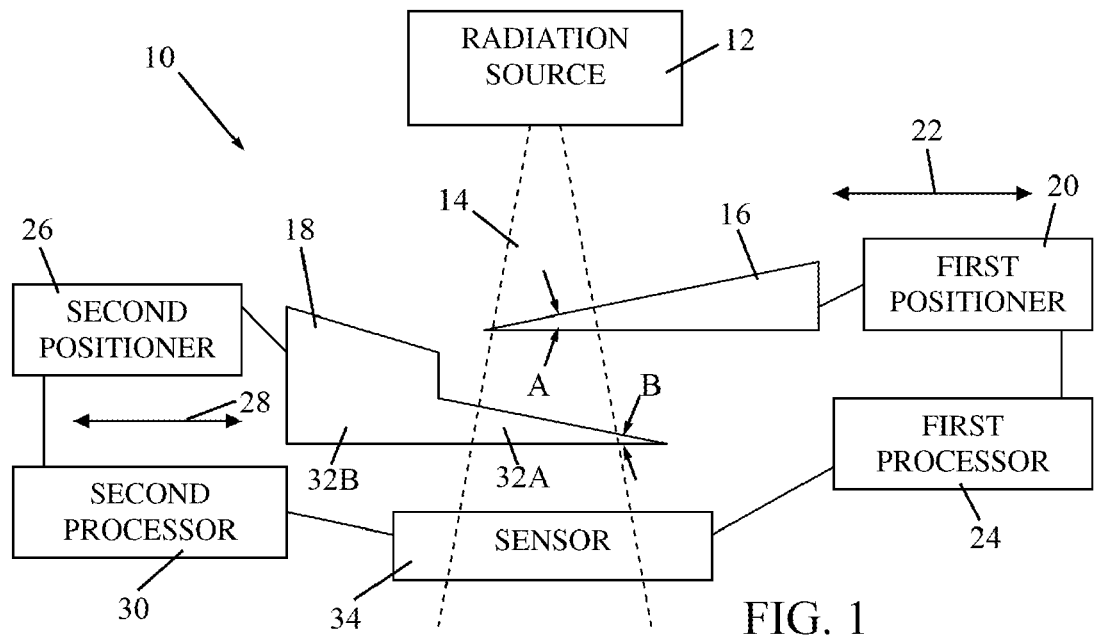
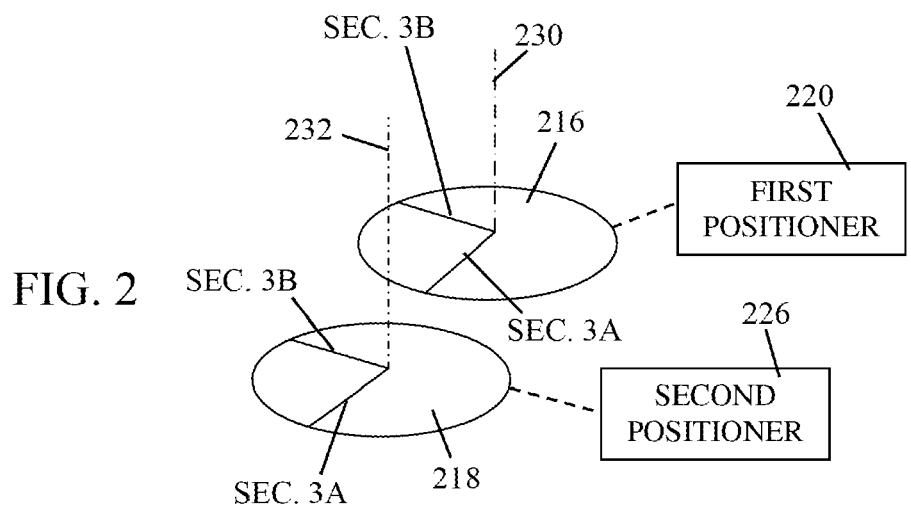
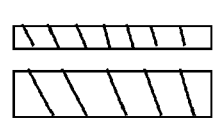 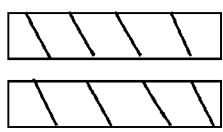
FIG. 3A    FIG. 3B

ATTENUATOR SYSTEM FOR BEAM MODULATION

FIELD OF THE INVENTION

The present invention generally relates to a system and method for radiation therapy or diagnostics with beam modulation, such as but not limited to, intensity modulated radiation therapy (IMRT) or diagnostics, and particularly to dynamic beam attenuators for such therapy or diagnostics, wherein the attenuating material and/or the attenuation length are variable.

BACKGROUND OF THE INVENTION

The intensity of the radiation beam used for radiotherapy is required to be time-invariant in some applications or time-varying in other applications. Temporal variation of beam intensity provides additional degree of freedom for stereotactic radiotherapy where beam apertures are varied with respect to gantry angle and/or desired segment. Variation of beam apertures and associated beam intensities can be done while the gantry is either rotating or stationary at a sequence of gantry orientations. The former is called Intensity modulated arc therapy (IMAT) and the latter is called "step-and-shoot" Intensity Modulated Radiation therapy (IMRT).

SUMMARY OF THE INVENTION

The present invention seeks to provide improved dynamic beam attenuators for therapy or diagnostics, wherein the attenuating material and/or the attenuation length are variable, as is described more in detail hereinbelow.

There is thus provided in accordance with an embodiment of the present invention an attenuator system for attenuating a radiation beam, including a first attenuating element placed in a path of a radiation beam for attenuation thereof, a second attenuating element also placed in the path of the radiation beam so as to form an attenuating cascade with the first attenuating element, a first positioner operatively connected to the first attenuating element, which moves the first attenuating element along a first direction, a first processor operatively connected to the first positioner for controlling motion of the first attenuating element, wherein a two-dimensional attenuation distribution of the first attenuating element varies linearly with respect to at least one coordinate.

In accordance with an embodiment of the present invention a two-dimensional attenuation distribution of the second attenuating element varies linearly with respect to at least one coordinate.

In accordance with an embodiment of the present invention the first and second attenuating elements form an attenuating cascade, wherein the attenuating cascade has an attenuation distribution depending on a position of the first attenuating element. The attenuation distribution of the attenuating cascade may be generally uniform over an area equal to a cross-section of the radiation beam for a range of positions of the first attenuating element. The two-dimensional attenuation distribution of the first and second attenuating elements with respect to the radiation beam may be spatially-continuous and non-uniform over an area significantly larger than that of the radiation beam.

The first attenuating element may have a cross-section coplanar with the radiation beam which is triangular in shape and which has an apex with a positive angle slope, and the second attenuating element may have a portion with a cross-section coplanar with the radiation beam which is triangular in shape and which has an apex with a negative angle slope. The magnitudes of the positive and negative angle slopes may be equal.

The attenuator system may further include a radiation sensor that senses attenuated radiation that passes through the first and second attenuating elements, the radiation sensor being in operative communication with the first processor, wherein temporal beam modulation is carried out by sensing a beam intensity with the radiation sensor and moving the first attenuating element with the first positioner.

The attenuator system may further incorporate a second positioner operatively connected to the second attenuating element, which moves the second attenuating element along a second direction, and a second processor operatively connected to the second positioner for controlling motion of the second attenuating element, In accordance with an embodiment of the present invention one of the first and second attenuating elements has two portions with different slopes and cross-sections.

In accordance with an embodiment of the present invention the first and second attenuating elements have cross-sections that vary along a Cartesian coordinate.

In accordance with another embodiment of the present invention the first and second attenuating elements have cross-sections that vary along a polar coordinate.

There is also provided in accordance with an embodiment of the present invention a radiotherapy system including a radiation beam source which emits a radiation beam, a first attenuating element placed in a path of the radiation beam for attenuation thereof, a second attenuating element also placed in the path of the radiation beam so as to form an attenuating cascade with the first attenuating element, a first positioner operatively connected to the first attenuating element, which moves the first attenuating element along a first direction, a first processor operatively connected to the first positioner for controlling motion of the first attenuating element, wherein a two-dimensional attenuation distribution of the first attenuating element varies linearly with respect to at least one coordinate.

There is also provided in accordance with an embodiment of the present invention a method for attenuating a radiation beam, including placing a first attenuating element in a path of a radiation beam for attenuation thereof, placing a second attenuating element also in the path of the radiation beam so as to form an attenuating cascade with the first attenuating element, and moving at least one of the first and second attenuating elements along a first or second direction, respectively, wherein a two-dimensional attenuation distribution of the first attenuating element varies linearly with respect to at least one coordinate.

The method may also include forming an attenuating cascade with the first and second attenuating elements form, wherein the attenuating cascade has an attenuation distribution depending on a position of the first attenuating element.

The method may further include carrying out temporal beam modulation by sensing a beam intensity and moving at least one of the first and second attenuating elements.

BRIEF DESCRIPTION OF THE DRAWINGS

The present invention will be understood and appreciated more fully from the following detailed description, taken in conjunction with the drawings in which:

FIG. 1 is a simplified illustration of a radiotherapy system with dynamic beam attenuators, constructed and operative in accordance with an embodiment of the present invention, wherein the attenuators are arranged for linear motion;

FIG. 2 is a simplified illustration of a radiotherapy system with dynamic beam attenuators, constructed and operative in accordance with another embodiment of the present invention, wherein the attenuators are arranged for rotational motion; and FIGS. 3A and 3B are sectional illustrations of the attenuators of FIG. 2 at two different angular positions.

DETAILED DESCRIPTION OF EMBODIMENTS

Reference is now made to FIG. 1, which illustrates an attenuator system 10 for use with a radiotherapy system, constructed and operative in accordance with a non-limiting embodiment of the present invention.

The radiotherapy system includes a radiation beam source 12, such as but not limited to, a LINAC, which emits a radiation beam 14. The radiation beam 14 can be shaped as a pencil-beam, fan-beam, cone-beam and other shapes. A first attenuating element 16 is placed in the path of beam 14 for attenuation thereof. A second attenuating element 18 is placed distal to first attenuating element 16 (i.e., further away from source 12) for further attenuation of beam 14. First and second attenuating elements 16 and 18 may be made of known attenuating materials, such as but not limited to, tungsten.

The two-dimensional attenuation distribution of first and second attenuating elements 16 and 18 with respect to the radiation beam may be spatially-continuous and non-uniform over an area significantly larger than that of radiation beam 14.

The first attenuating element 16 is operatively connected to a first positioner 20 (such as a motor, linear actuator and the like), which moves first attenuating element 16 along a first direction, such as along a first axis 22, which may be perpendicular to the axis of beam 14. A first processor 24 is operatively connected to first positioner 20 for controlling the motion of first attenuating element 16. Similarly, second attenuating element 18 is operatively connected to a second positioner 26 (such as a motor, linear actuator and the like), which moves second attenuating element 18 along a second direction, such as along a second axis 28, which may be perpendicular to the axis of beam 14. A second processor 30 is operatively connected to second positioner 26 for controlling the motion of second attenuating element 18.

The first attenuating element 16 has a cross-section (taken in the same plane as beam 14, as shown in FIG. 1) which is triangular in shape, having an apex with a positive angle slope designated A. (As in conventional mathematical notation, positive angles are measured counterclockwise from the reference horizontal axis, whereas negative angles are measured clockwise.) The second attenuating element 18 has a portion 32 with a cross-section (taken in the same plane as beam 14, as shown in FIG. 1) which is triangular in shape, having an apex with a negative angle slope designated -B. In a preferred embodiment, the magnitudes of A and B are equal.

Accordingly, the attenuating material (or attenuation length) varies continuously along at least one coordinate (in the illustrated embodiment, linear, that is, along a Cartesian-coordinate axis 22 or 28). Moving first or second attenuator 16 or 18 in a direction generally perpendicular to the beam (along axis 22 or 28) shifts the two-dimensional attenuating distribution and provides temporal beam modulation.

A radiation monitor 34, referred to as radiation sensor 34, may sense (measure) the attenuated radiation that passes through the attenuators to the target. Radiation sensor 34 is in operative communication with first and second processors 24 and 30. Temporal beam modulation may be used for beam intensity stabilization by sensing the instantaneous intensity drift with radiation sensor 34 and compensating with a proper attenuator positioning by moving first and/or second attenuating elements 16/18 with their positioners 20/26. The present invention may also be used for conformal radiation, where different intensities are associated with discrete or continuously varying orientations.

For further variety of attenuation, as seen in FIG. 1, one of the first and second attenuators 16 and 18, such as second attenuator 18, can have two portions 32A and 32B with different slopes and cross-sections.

Thus, a combination of spatial uniformity (over an area compatible with the beam cross-section) and temporal variation is achieved by the cascading attenuators 16 and 18. In the preferred embodiment wherein the magnitudes of angles A and B are equal, the two respective attenuation distributions are linear and have the same slope but in opposite directions. This results in a combined uniform attenuation irrespective of the relative positions of first and second attenuators 16 and 18.

It is noted that the invention can be carried out with one of the attenuators maintained stationary, and moving just one of them relative to radiation beam 14. The advantage of a stationary attenuating object is its small size being equal to the beam cross-section while the size of the moving attenuating object can be an order of magnitude larger.

Uniformity and temporal variation can be achieved by an attenuator's variation (and corresponding motion) along a single coordinate. In the embodiment of FIG. 1, the variation is linear along a Cartesian coordinate. Referring to FIGS. 2 and 3A-3B, it is seen first and second attenuating elements 216 and 218 can have cross-sections that vary along a polar coordinate. In such an embodiment, first and second positioners 220 and 226 rotate first and second attenuating elements 216 and 218 about first and second rotation axes 230 and 232, respectively.

The scope of the present invention includes both combinations and subcombinations of the features described hereinabove as well as modifications and variations thereof which would occur to a person of skill in the art upon reading the foregoing description and which are not in the prior art.

What is claimed is:

1. An attenuator system for attenuating a radiation beam, comprising:

a first attenuating element placed in a path of a radiation beam for attenuation thereof;

a second attenuating element also placed in said path of said radiation beam so as to form an attenuation cascade with said first attenuating element;

a first positioner operatively connected to said first attenuating element, which moves said first attenuating element along a first direction; and a first processor operatively connected to said first positioner for controlling motion of said first attenuating element;

wherein a two-dimensional attenuation distribution of said first attenuating element varies linearly with respect to at least one coordinate, and wherein one of said first and second attenuating elements has two portions with different slopes and cross-sections.

2. The attenuator system according to claim 1, wherein a two-dimensional attenuation distribution of said second attenuating element varies linearly with respect to at least one coordinate.

3. The attenuator system according to claim 1, wherein said first and second attenuating elements form an attenuating cascade, wherein the attenuating cascade has an attenuation distribution depending on a position of said first attenuating element.

4. The attenuator system according to claim 3, wherein the attenuation distribution of the attenuating cascade is generally uniform over an area equal to a cross-section of the radiation beam for a range of positions of said first attenuating element.

5. The attenuator system according to claim 1, further incorporating a second positioner operatively connected to said second attenuating element, which moves said second attenuating element along a second direction; and a second processor operatively connected to said second positioner for controlling motion of said second attenuating element.

6. The attenuator system according to claim 5, wherein said first direction and said second direction are parallel to each other.

7. The attenuator system according to claim 5, wherein said first direction and said second direction are both perpendicular to said radiation beam.

8. The attenuator system according to claim 1, wherein said first attenuating element has a cross-section coplanar with the radiation beam which is triangular in shape and which has an apex with a positive angle slope, and said second attenuating element has a portion with a cross-section coplanar with the radiation beam which is triangular in shape and which has an apex with a negative angle slope.

9. The attenuator system according to claim 8, wherein magnitudes of the positive and negative angle slopes are equal.

10. The attenuator system according to claim 1, further comprising a radiation sensor that senses attenuated radiation that passes through said first and second attenuating elements, said radiation sensor being in operative communication with said first processor, wherein temporal beam modulation is carried out by sensing a beam intensity drift with said radiation sensor and compensating by moving said first attenuating element by said first positioner.

11. The attenuator system according to claim 1, wherein said first and second attenuating elements have cross-sections that vary along a Cartesian coordinate.

12. The attenuator system according to claim 1, wherein said first and second attenuating elements have cross-sections that vary along a polar coordinate.

13. A radiotherapy system comprising:
a radiation beam source which emits a radiation beam;
a first attenuating element placed in a path of the radiation beam for attenuation thereof;
a second attenuating element also placed in said path of said radiation beam so as to form an attenuating cascade;
a first positioner operatively connected to said first attenuating element, which moves said first attenuating element along a first direction; and
a first processor operatively connected to said first positioner for controlling motion of said first attenuating element;
wherein a two-dimensional attenuation distribution of said first attenuating element varies linearly with respect to at least one coordinate, and wherein one of said first and second attenuating elements has two portions with different slopes and cross-sections.

14. The radiotherapy system according to claim 13, further comprising a radiation sensor that senses attenuated radiation that passes through said first and second attenuating elements, said radiation sensor being in operative communication with said first processor, wherein temporal beam modulation is carried out by sensing a beam intensity with said radiation sensor and moving said first attenuating element with said first positioner.

15. A method for attenuating a radiation beam, comprising:
placing a first attenuating element in a path of a radiation beam for attenuation thereof;
placing a second attenuating element also in said path of said radiation beam so as to form an attenuating cascade; and
moving said first attenuating element along a first direction;
wherein a two-dimensional attenuation distribution of said first attenuating element varies linearly with respect to at least one coordinate, and wherein one of said first and second attenuating elements has two portions with different slopes and cross-sections.

16. The method according to claim 15, comprising forming an attenuating cascade with said first and second attenuating elements form, whereas a second positioner is operatively connected to said second attenuating element, which moves said second attenuating element along a second direction; and a second processor is operatively connected to said second positioner for controlling motion of said second attenuating element; and wherein the attenuating cascade has an attenuation distribution depending on a position of said first attenuating element.

17. The method according to claim 15, further comprising carrying out temporal beam modulation by sensing a beam intensity and moving at least one of said first and second attenuating elements.

* * * * *